United States Patent [19]

Lebo

[11] 3,960,718
[45] June 1, 1976

[54] METHOD AND APPARATUS FOR TREATING LIQUID SEWAGE AND WASTE
[76] Inventor: Willis R. Lebo, 6510 21st Ave., NE., Tacoma, Wash.
[22] Filed: Aug. 5, 1974
[21] Appl. No.: 494,742

[52] U.S. Cl. .................................. 210/14; 210/15; 261/79 A; 71/13
[51] Int. Cl.² .......................................... C02C 1/08
[58] Field of Search .............. 210/512 R, 15, 18, 14, 210/10, 198, 64, 61, 59, 7, 6, 84, 197, 221, 220, 63; 71/9, 12, 13, 24; 261/77, 121 R, 79 A

[56] References Cited
UNITED STATES PATENTS

| | | | |
|---|---|---|---|
| 3,271,304 | 9/1966 | Valdespino et al. | 210/14 |
| 3,390,076 | 6/1968 | Dubach | 210/15 |
| 3,476,682 | 11/1969 | Albersmeyer | 210/197 |
| 3,574,331 | 4/1971 | Kurosawa et al. | 210/15 |
| 3,695,439 | 10/1972 | Dupre | 210/197 |
| 3,733,263 | 5/1973 | Mandt | 210/14 |
| 3,758,287 | 9/1973 | Scheel | 71/12 |
| 3,772,187 | 11/1973 | Othmer | 210/8 |
| 3,801,501 | 4/1974 | Kennedy | 210/61 |

Primary Examiner—Charles N. Hart
Assistant Examiner—Benoit Castel
Attorney, Agent, or Firm—Seed, Berry, Vernon & Baynham

[57] ABSTRACT

Liquid sewage and waste, such as manure and/or sewage sludge, are treated to destroy pathogenic bacteria and remove offensive odors to make the material usable as a plant nutrient and soil conditioner. The liquid sewage is thoroughly aerated within a cone-shaped, pressurized vessel by injection of a jet of compressed air tangentially to the side walls of the vessel into contact with the liquid sewage. The vortex motion and agitation created by injection of the compressed air disintegrates the larger solids of the sewage or sludge so that the compressed air can permeate the material to a greater degree. A head of compressed air is built up above the liquid level in the pressurized vessel, which, on opening of a discharge valve in the lower end of the pressurized vessel, forces the contents of the vessel through an outlet pipe connected to the vessel through the discharge valve. The material may be used as is or discharged onto a pile of sawdust, ground bark or straw for composting. After an adequate composting period, the material can be packaged for sale or used directly as a soil amendment and fertilizer. To insure thorough sterilization of the material in the case of sewage waste, a metered amount of sulfuric acid is injected into the material being treated to lower the pH of the material to pH 3.0 or less. After an exposure of several minutes to this low pH environment to destroy pathogenic bacteria, the material is treated with a neutralizing agent to increase the pH to an optimum value for use as a plant food.

3 Claims, 2 Drawing Figures

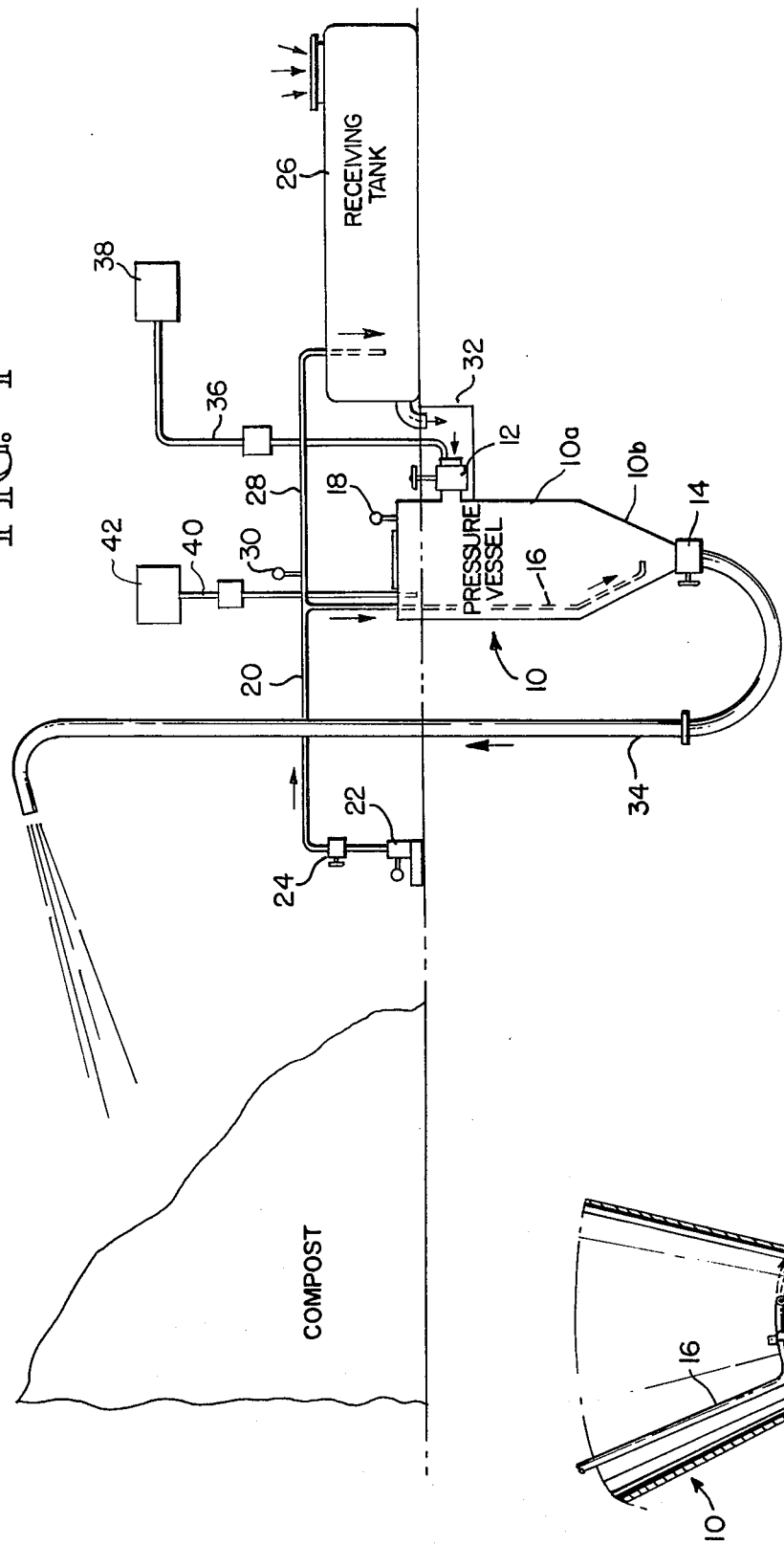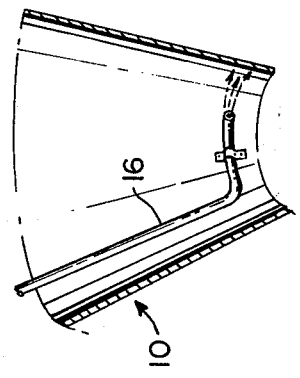

METHOD AND APPARATUS FOR TREATING LIQUID SEWAGE AND WASTE

BACKGROUND OF THE INVENTION

1. Field of the Invention

This invention relates to a method and apparatus for treating liquid sewage and waste to deodorize and destroy pathogenic bacteria contained therein.

2. Prior Art Relating to the Disclosure

Many municipal sewage treatment processes in use today are encountering severe disposal problems with regard to sewage sludge. Because of the increasingly stringent water pollution regulations, sewage sludge can no longer be dumped into water bodies. It is also becoming increasingly difficult to find suitable landfill sites for disposal of sewage sludge. Generally, the sewage sludge has an unacceptable bacteria content, and, for that reason, cannot be directly used as a soil fertilizer or amendment without further treatment.

Numerous methods are known for treatment of waste. For example, U.S. Pat. No. 3,772,188 discloses a treatment apparatus and method for treating sewage and waste using a pressurized vessel which receives high purity oxygen or ozone in the upper portion thereof. A stream of sewage is injected into the oxygen-rich atmosphere against a comminutor device which breaks the sewage into small particles to allow it to quickly absorb the oxygen under pressure and provide rapid biological chemical oxidation and ozone sterilization.

U.S. Pat. No. 3,728,254 discloses a method and apparatus for production of fertilizer using a modified activated sludge treatment process. Organic kitchen waste, yard and garden trimmings and trash are comminuted and introduced into sanitary sewage lines for conveying to the treatment plant as a combined effluent. The combined effluent is directed into an aeration tank modified to provide supplemental aeration sufficient to biochemically decompose the solids and form a mixed liquid effluent rich in plant nutrients.

U.S. Pat. No. 3,574,331 discloses an aeration tank for waste treatment wherein the initial contact between gaseous oxygen and waste material is made at hydrostatic pressures of not less than 9 psi using an open, vertically elongated aeration tank.

U.S. Pat. No. 3,758,287 discloses a process of treating organic waste to sterilize, deodorize and dewater the waste utilizing the heat generated by the chemical reaction of magnesium oxide and sulfuric acid.

SUMMARY OF THE INVENTION

A cyclic method and apparatus are disclosed for treating manures, raw sewage or sewage sludge to destroy or reduce to an innocuous level all pathogenic bacteria contained therein and to deodorize the material, making it usable as a plant nutrient and soil conditioner as is or composted with materials such as straw, wood shavings, sawdust, ground bark, wood chips or other such material. The liquid raw sewage or sewage sludge is fed into a conical pressurization vessel where the material is thoroughly aerated by injecting a jet of compressed air into the material in the vessel. The air is injected tangentially to the side walls of the lower conical portion of the tank to not only aerate the material therein but also to disintegrate the larger solids in the material by action of the air stream against the solids and impact of the solids against the walls of the tank, allowing the air to thoroughly permeate the material. Air injected into the tank develops hydrostatic pressure above the liquid level in the vessel which increases the solubility of the air in the material to a greater degree than if injected at ambient pressure.

To insure thorough sterilization, a metered amount of sulfuric acid is injected into the material either before feeding of the material into the pressurized vessel or simultaneously with injection of the compressed air into the vessel to lower the pH of the material to pH 3.0 or less. After sufficient exposure to this low pH environment, a neutralizing material, such as ammonia or lime, is added to raise the pH to an optimum value for use as a plant food.

It is a primary object of the invention to provide a method and apparatus for treating liquid sewage and waste wherein the liquid material is moved by air pressure and without the use of pumps, which generally require considerable maintenance costs.

It is a further object of the invention to provide a method and apparatus for treating liquid sewage and waste wherein the material is thoroughly aerated, deodorized and sterilized efficiently and at relatively low cost.

BRIEF DESCRIPTION OF THE DRAWINGS

FIG. 1 is a schematic of the system for the treatment of raw sewage, sewage sludge and/or manures; and FIG. 2 is a partial view of the nozzle injecting compressed air into the pressure vessel.

DESCRIPTION OF THE PREFERRED EMBODIMENTS

The method and apparatus disclosed make use of air pressure not only for aeration of the sewage and/or waste but also to break up and disintegrate solids contained therein for thorough aeration thereof at low capital cost. In addition, the method and equipment make use of a combination of chemical treatment and aeration to thoroughly deodorize and sterilize sewage waste before discharge.

The material to be treated may be raw sewage, sewage sludge, cesspool and septic waste or manures. In the case of manures, aeration to deodorize and, to some extent, sterilize the manures is all that is required. For sewage waste and sewage sludge, chemical treatment to destroy pathogenic bacteria is necessary.

The pressure vessel is a conical vessel 10 having an upper cylindrical portion 10a and an integral lower conical portion 10b. Material to be treated is received into the vessel through an inlet opening near the upper end of the vessel and discharged through an outlet opening in the lower end of the vessel. Both the inlet and outlet openings are provided with valves 12 and 14, respectively. When the pressure vessel is sunk into the ground, as illustrated in FIG. 1, valve 14 is remotely operated.

An air line 16 extends down into the vessel and terminates near the lower end thereof. The terminating end of the air line is twisted and provided with a nozzle, as indicated in FIG. 2, to inject air into the pressure vessel tangentially to the side walls 10b. A pressure gauge 18 is provided for monitoring of the air pressure within the pressure vessel. The pressurized air is supplied to air line 16 through air line 20 by air compressor 22. A valve 24, connected in the air line 20, controls the air pressure injected into the pressure vessel.

The material to be treated may be fed directly to the pressure vessel from a sewage treatment plant or may first be received in a receiving tank 26, as indicated in FIG. 1. The receiving tank may be connected to the same source of pressurized air through air line 28 to pressurize the tank and force the material into the pressure vessel 10, or the material may be allowed to flow by gravity into the pressure vessel. A second pressure gauge 30 may be provided to monitor the air pressure in air lines 20 and 28. Air pressure built up above the liquid level in the receiving tank forces the material from the receiving tank through line 32 and valve 12 into the pressure vessel. Once in the pressure vessel, the outlet and inlet valves are closed and pressurized air injected through air line 16 to not only thoroughly aerate the material in the vessel but also to thoroughly disintegrate larger solids in the material. The injected air rises above the liquid level in the pressure vessel and forms a head at a pressure of from 4 to 15 psi above the liquid level in the vessel. Location of the air jet in the conical portion of the vessel augments the turbulence imparted to the treated material. Greater than atmospheric pressure within the pressure vessel also increases the solubility of the air in the material so that it permeates it to a greater degree than if at ambient temperature.

Injection of air into the pressurized vessel is terminated after a suitable treatment time of from 10 to 15 minutes and discharge valve 14 opened. A discharge conduit 34 is connected to the discharge opening of the pressure vessel to convey the discharged material for use as is or to a location for spraying onto materials such as peat moss, ground bark, sawdust, straw or other suitable material for composting. Once the pressure vessel is emptied, the discharge valve is closed and the inlet valve opened to receive additional material to be treated.

Aeration of the liquid material in the pressure vessel under the conditions described results in total elimination of the odor of the material. When treating manures, such as cow manure or poultry manure, the aerated material may be used as is or sprayed onto a material for composting. The composted material, after a suitable composting time, is used for a soil amendment or fertilizer. When treating municipal sewage waste or cesspool or septic tank waste, the pathogenic bacteria contained therein must be effectively destroyed before it can be used as a soil amendment or fertilizer.

In this regard, it was found that sulfuric acid injected into the material on entry into or while in the pressure vessel at the time of aeration in sufficient amounts to reduce the pH of the liquid solution to about 3.0 or less results in almost total destruction of the pathogenic bacteria contained in the sewage waste. Referring to FIG. 1, the required amount of sulfuric acid may be injected through line 36 from a holding vessel 38 into the pressure vessel. Preferably, the sulfuric acid is introduced directly into the tank at the inlet end of the vessel where the flow of material in the vessel may be metered relative to the amount of acid being introduced to give precise control of the amount of sulfuric acid injected into the material being treated. After a suitable dwell time at the low pH, from 10 to 15 minutes, the material is preferably neutralized to pH 6–7 by the addition of ammonia, quicklime, limestone, hydrated lime or other suitable neutralizing agent into the material through line 40 into the vessel from a holding tank 42. Ammonia is preferred for neutralization of the sulfuric acid to give ammonium sulfate, an excellent fertilizing material. Alternatively, the neutralizing agent may be injected into the treated material as it is being discharged from the pressure vessel through the outlet pipe.

The method and system described above completely deodorize the waste being treated with only a few minutes aeration time. Introduction of compressed air into the lower portion of the conical section of the pressure vessel with the terminating end of the air line configured to produce a swirling motion and extreme turbulence in the liquid being treated causes generation of minute air bubbles which rise to the liquid surface in the pressure vessel. The high air surface-to-volume ratio and pressure in the pressure vessel efficiently transfer dissolved oxygen to the liquid being treated. Additionally, the violent agitation created by injection of compressed air into the pressure vessel in the manner described has a mascerating effect on the material being treated, resulting in break-up of larger solids so that there is complete treatment of the material. This is particularly advantageous during acidification with sulfuric acid to sterilize the material. Following the addition of sulfuric acid with a period of aeration accomplishes complete mixing of the acid with the material being treated.

The method described herein may be adapted to the treatment of municipal sewage in place of the conventional municipal sewage treatment plant. Specifically, municipal sewage en route to a treatment plant through sewage lines can be put through the method herein described and then be used for fertilization and irrigation.

EXAMPLE 1

Liquid cow manure was fed into a pressure vessel 4 feet in diameter and 8 feet in height of the configuration shown in FIG. 1. Compressed air was injected into the vessel through a ¾ inch internal diameter air line terminating about 6 inches above the discharge outlet of the pressure vessel. The entering liquid cow manure had a dissolved oxygen content of 0.5 parts per million. After aeration using compressed air for 10 to 15 minutes, the dissolved oxygen content of the material was 4.0 parts per million. Sulfuric acid was then added to the material being treated in an amount sufficient to decrease the pH of the material to pH 2.4. Aeration was then continued for 10 to 15 minutes. The dissolved oxygen content was measured and was 5.6 parts per million. The material was then ejected from the pressure vessel onto a pile of sawdust and the sawdust composted for a period ranging from 60 to 90 days. Temperatures of up to 150°F. were measured within the pile. The composted material was odor free and the bacteria count low enough that it presented no health problem.

EXAMPLE 2

Sewage collected from septic tanks were aerated for 15 minutes as described in Example 1. Then 12 quarts of sulfuric acid per 1000 gallons of sewage were added and the material was again aerated for 15 additional minutes. Samples were taken of the sewage (1) before treatment, (2) after aeration and (3) after acidification and additional aeration. Analysis of the samples gave the following results:

| Sample Number | Standard Plate Count per ml. | Coliform Count M.P.N. per 100 ml. of sample | Fecal Coliform M.P.N. per 100 ml. of sample | pH |
| --- | --- | --- | --- | --- |
| 1 | 5,000,000 | 24,000,000 | 11,000,000 | 6.8 |
| 2 | 5,500,000 | 11,000,000 | 2,400,000 | 6.9 |
| 3 | 110,000 | 150,000 | less/30 | 2.8 |

The embodiments of the invention in which a particular property or privilege is claimed are defined as follows:

1. A method of treating liquid material consisting essentially of sewage and/or manures having solids therein to make the liquid material usable as a plant nutrient and soil conditioner, comprising:

feeding the liquid material into a cone-shaped pressure vessel, injecting a stream of pressurized oxygen-containing gas into the pressure vessel near the lower end thereof and tangential to the side walls of the conical portion of the vessel to impart a centrifugal motion to the liquid material and impinge the pressurized gas against the solids in the liquid material with sufficient force to break the solids into small particles, the gas thoroughly aerating the material and pressurizing the vessel with the oxygen-containing gas to a pressure ranging from 4 to 15 psi above the liquid level in the pressure vessel, injecting sulfuric acid into the liquid material in an amount sufficient to adjust the pH of the liquid material to a pH of 3.0 or less for sterilization thereof, and readjusting the pH to approximately 6 to 7, and discharging the liquid material from the vessel by the gas pressure formed above the liquid level in the vessel onto a compost material selected from the group consisting of sawdust, ground bark, peatmoss, straw and wood chips.

2. The method of claim 1 wherein the sulfuric acid is introduced into the liquid material prior to introduction of the material into the pressure vessel.

3. The method of claim 1, including metering the rate of flow of liquid material fed to the pressure vessel and injecting said sulfuric acid into the liquid material being treated relative to the amount of liquid material in the pressure vessel.

* * * * *